United States Patent [19]

Williams

[11] Patent Number: 5,032,596
[45] Date of Patent: Jul. 16, 1991

[54] TREATMENT OF DISORDERS ASSOCIATED WITH PULMONARY HYPERTENSION AND/OR RIGHT HEART FAILURE

[75] Inventor: Andrew J. Williams, Epsom, England

[73] Assignee: Beecham Group p.l.c., Middlesex, England

[21] Appl. No.: 215,243

[22] Filed: Jul. 5, 1988

[30] Foreign Application Priority Data

Jul. 7, 1987 [GB] United Kingdom ............... 8715943
Aug. 6, 1987 [GB] United Kingdom ............... 8718585

[51] Int. Cl.$^5$ ................ A61K 31/35; A61K 31/40; A61K 31/44
[52] U.S. Cl. ........................ 514/302; 514/422; 514/456
[58] Field of Search .................. 514/302, 422, 456

[56] References Cited

U.S. PATENT DOCUMENTS

| | | | |
|---|---|---|---|
| 4,738,963 | 4/1988 | Hamilton et al. | 514/222 |
| 4,772,603 | 9/1988 | Evans | 514/422 |
| 4,782,083 | 11/1988 | Cassidy et al. | 514/422 |
| 4,786,639 | 11/1988 | Evans | 514/422 |
| 4,812,459 | 3/1989 | Evans et al. | 514/302 |

FOREIGN PATENT DOCUMENTS 0173848 3/1986 European Pat. Off. ........... 514/422

Primary Examiner—Stanley J. Friedman
Attorney, Agent, or Firm—Hopgood, Calimafde, Kalil, Blaustein & Judlowe

[57] ABSTRACT

A method for the treatment and/or prophylaxis of disorders associated with pulmonary hypertension and/or disorders associated with right heart failure, in mammals, which method comprises administering to the mammal in need of such treatment and/or prophylaxis an effective and/or prophylactic, non-toxic, amount of a compound of formula (I):

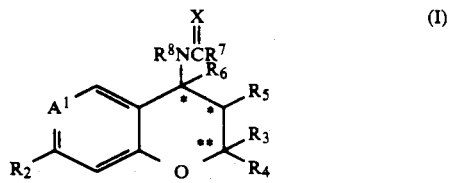

(I)

wherein $A^1$ represents $CR_1$, N or $N^+$—$O^-$;
when $A^1$ represents N or $N^+$—$O^-$, $R^2$ represents hydrogen;
when $A^1$ represents $CR_1$ then:
either;
one of $R_1$ and $R_2$ is hydrogen and the other is a group $R^a$ wherein $R^a$ is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkylsulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl or amionosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —$C(C_{1-6}$ alkyl)NOH or —$C(C_{1-6}$ alkyl)NHN$_2$, or;
one of $R_1$ and $R_2$ is nitro, cyano or $C_{1-3}$ alkylcarbonyl and the other is a group $R^b$ wherein $R^b$ is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen, hydroxy, $C_{1-6}$ alkoxy or $C_{1-7}$ acyloxy and $R_6$ is hydrogen or $R_5$ and $R_6$ together are abond;
$R_7$ is hydrogen, $C_{1-6}$ alkyl optionally substituted by hydroxy, $C_{1-6}$ alkoxy, $C_{1-6}$ alkoxycarbonyl or carboxy, $C_{1-6}$ alkyl substituted by halogen, or $C_{2-6}$ alkenyl; aryl or heteroaryl either being optionally substituted by one or more groups or atoms selected from the class of $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl groups;
$R_8$ is hydrogen or $C_{1-6}$ alkyl; or
$R_7$ and $R_8$ are joined together to form $C_{3-4}$ polymethylene or —$CH_2$— $(CH_2)_n$—$Z$—$(CH_2)_m$— wherein m and n represent zero or 1 or 2 such that m+n is 1 or 2, and Z is oxygen, sulphur or $NR_9$ wherein $R_9$ is hydrogen, $C_{1-9}$ alkyl, $C_{2-7}$ alkanoyl, phenyl $C_{1-4}$ alkyl, naphthylcarbonyl, phenylcarbonyl or benzylcarbonyl optionally substituted in the phenyl or naphthyl ring by one or two $C_{1-6}$ alky, $C_{1-6}$ alkoxy or halogen; mono- or bi-cyclicheteroarylcarbonyl;
X is oxygen or sulphur;
or a pharmaceutically acceptable salt thereof, or a pharmaceutically acceptable solvate thereof.

12 Claims, No Drawings

TREATMENT OF DISORDERS ASSOCIATED WITH PULMONARY HYPERTENSION AND/OR RIGHT HEART FAILURE

The present invention relates to a method for the treatment and/or prophylaxis of disorders associated with pulmonary hypertension.

European Patent Publication Nos. 76075, 91748, 93535, 95316, 107423, 120426, 120427, 126311, 126350, 126367 and 138134 describe classes of chromanols, chromenes and chromans having anti-hypertensive activity.

It has now been discovered that compounds of this type have a mechanism of action which indicates that they are of potential use in the treatment and/or prophylaxis of disorders associated with pulmonary hypertension and of disorders associated with right heart failure.

Accordingly, the present invention provides a method for the treatment and/or prophylaxis of disorders associated with pulmonary hypertension and/or disorders associated with right heart failure, in mammals, such as humans, which method comprises administering to the mammal in need of such treatment and/or prophylaxis an effective and/or prophylactic, non-toxic, amount of a compound of formula (I):

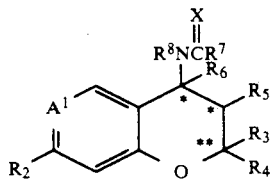

wherein $A^1$ represents $CR_1$, N or $N^+$—$O^-$;
when $A^1$ represents N or $N^+$—$O^-$, $R^2$ represents hydrogen;
when $A^1$ represents $CR_1$ then:
either;
one of $R_1$ and $R_2$ is hydrogen and the other is a group $R^a$ wherein $R^a$ is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —$C(C_{1-6}$ alkyl)NOH or —$C(C_{1-6}$ alkyl)$NNH_2$,
or;
one of $R_1$ and $R_2$ is nitro, cyano or $C_{1-3}$ alkylcarbonyl and the other is a group $R^b$ wherein $R^b$ is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;

either $R_5$ is hydrogen, hydroxy, $C_{1-6}$ alkoxy or $C_{1-7}$ acyloxy and $R_6$ is hydrogen or $R_5$ and $R_6$ together are a bond;
$R_7$ is hydrogen, $C_{1-6}$ alkyl optionally substituted by hydroxy, $C_{1-6}$ alkoxy, $C_{1-6}$ alkoxycarbonyl or carboxy, $C_{1-6}$ alkyl substituted by halogen, or $C_{2-6}$ alkenyl; aryl or heteroaryl either being optionally substituted by one or more groups or atoms selected from the class of $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl groups;
$R_8$ is hydrogen or $C_{1-6}$ alkyl; or
$R_7$ and $R_8$ are joined together to form $C_{3-4}$ polymethylene or —$CH_2$—$(CH_2)_n$—$Z$—$(CH_2)m$— where m and n represent zero or 1 or 2 such that m+n is 1 or 2, and Z is oxygen, sulphur or $NR_9$ wherein $R_9$ is hydrogen, $C_{1-9}$ alkyl, $C_{2-7}$ alkanoyl, phenyl $C_{1-4}$ alkyl, naphthylcarbonyl, phenylcarbonyl or benzylcarbonyl optionally substituted in the phenyl or naphthyl ring by one or two $C_{1-6}$ alkyl, $C_{1-6}$ alkoxy or halogen; mono- or bi-cyclicheteroarylcarbonyl;
X is oxygen or sulphur;
or a pharmaceutically acceptable salt thereof, or a pharmaceutically acceptable solvate thereof.

Preferably, $A^1$ is $CR_1$.

When one of $R_1$ and $R_2$ is hydrogen and the other is $R^a$, then $R^a$ is preferably selected from the class of $C_{1-6}$ alkylcarbonyl, $C_{1-6}$ alkoxycarbonyl, nitro or cyano. In particular, when one of $R_1$ and $R_2$ is hydrogen and the other is $R^a$, then $R^a$ is preferably acetyl, nitro or cyano, especially nitro or cyano.

When one of $R_1$ and $R_2$ is hydrogen, it is preferred that $R_2$ is hydrogen.

When one of $R_1$ and $R_2$ is nitro, cyano or $C_{1-3}$ alkylcarbonyl and the other is $R^b$, then $R^b$ is preferably, amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl and the other is $R^b$, then $R^b$ is amino, methylamino, dimethylamino or acetylamino. Most preferably, one of $R_1$ and $R_2$ is nitro or cyano, especially cyano, and the other is $R^b$ when $R^b$ is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alkyl-containing groups for $R_1$ or $R_2$ are, preferably, methyl or ethyl.

Preferably, $R_1$ is $R^a$ and $R^a$ cyano.

Preferably, $R_2$ is hydrogen.

Most preferably, $R_1$ is $R^a$, $R^a$ is cyano and $R_2$ is hydrogen.

Preferably, $R_3$ and $R_4$ are both $C_{1-4}$ alkyl, in particular both $R_3$ and $R_4$ are methyl.

When $R_5$ is $C_{1-6}$ alkoxy and $R_6$ is hydrogen, preferred examples of $R_5$ include methoxy and ethoxy, of which methoxy is more preferred. When $R_5$ is $C_{1-7}$ acyloxy and $R_6$ is hydrogen, a preferred class of $R_5$ is unsubstituted carboxylic acyloxy, such as unsubstituted aliphatic acyloxy or benzoyloxy. However, it is preferred that $R_5$ and $R_6$ together are a bond, or $R_5$ and $R_6$ are both hydrogen, or, in particular, that $R_5$ is hydroxy and $R_6$ is hydrogen.

Suitable values for $R_8$, when $R_7$ and $R_8$ are not joined together include hydrogen, methyl, ethyl, n- and isopropyl, n-, sec- and tert-butyl. Favourably, $R_8$ is hydrogen or methyl, most preferably hydrogen.

Suitable values for $R_7$ then include hydrogen, methyl, ethyl, n- and iso-propyl, n-, sec- and tert-butyl, methyl or ethyl substituted by carboxy or chloro, vinyl, prop-1-enyl, prop-2-enyl, 1-methylvinyl, but-1-enyl, but-2-enyl, but-3-enyl, 1-methylenepropyl, 1-methylprop-1-enyl, 1-methylprop-2-enyl, (in their E and Z forms where stereoisomerism exists), and methyl or ethyl terminally substituted by hydroxy or methoxy. Favourably $R_7$ is methyl, ethyl, n- or iso-propyl or vinyl, in particular, methyl, hydroxymethyl and methoxymethyl. Preferably $R_7$ is methyl.

Examples of $R_7$ aryl include phenyl and naphthyl of which phenyl is preferred.

A sub-class of $R_7$ heteroaryl is 5- or 6-membered monocyclic or 9- or 10-membered bicyclic heteroaryl of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different.

Examples of 5- or 6-membered monocyclic heteroaryl containing one, two or three heteroatoms which are selected from the class of oxygen, nitrogen and sulphur include furanyl, thiophenyl, pyrrolyl, oxazolyl, thiazolyl, imidazolyl and thiadiazolyl, and pyridinyl, pyridazinyl, pyrimidinyl, pyrazinyl and triazinyl. Preferred examples of such groups include furanyl, thiophenyl, pyrrolyl and pyridyl, in particular 2- and 3-furanyl, 2- and 3-pyrrolyl, 2- and 3-thiophenyl, and 2-, 3- and 4-pyridyl.

Examples of 9- or 10-membered bicyclic heteroaryl containing one, two or three heteroatoms which are selected from the class of oxygen, nitrogen and sulphur include benzofuranyl, benzothiophenyl, indolyl and indazolyl, quinolinyl and isoquinolinyl, and quinazoninyl. Preferred examples of such groups include 2- and 3-benzofuranyl, 2- and 3-benzothiophenyl, and 2- and 3-indolyl, and 2- and 3-quinolinyl.

Preferably, the number of groups or atoms for optional substitution of aryl or heteroaryl is one, two, three or four.

Preferred examples of the groups or atoms for optional substitution of aryl or heteroaryl include methyl, methoxy, hydroxy, chloro, fluoro, nitro or cyano.

When $R_7$ and $R_8$ are joined together they are preferably $C_3$ or $C_4$ polymethylene or $-CH_2-(CH_2)_{n1}-Z-(CH_2)_{m1}-$ where $n^1$ is 0 or 1 and $m^1$ is 0 or 1.

Preferably, $R_7$ and $R_8$ are joined together.

Preferably, $R_7$ and $R_8$ together represent $C_3$-polymethylene.

X is preferably oxygen.

There is a favourable group of compounds within formula (I) of formula (II):

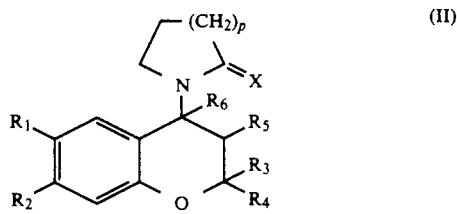

(II)

wherein p is 1 or 2 and the remaining variables are as defined with respect to the compound of formula (I), or a pharmaceutically acceptable salt thereof, or a pharmaceutically acceptable solvate thereof.

Preferably p is 1.

Preferably in the compound of formula (II), $R_1$ is cyano, $R_2$ is hydrogen, $R_3$ is $C_{1-4}$ alkyl, especially methyl, $R_4$ is $C_{1-4}$ alkyl, especially methyl, $R_5$ is hydroxy, $R_6$ is hydrogen, X is oxygen aDd p is 1.

In a particularly preferred aspect of the present invention the compound of formula (I) is 6-cyano-3,4-dihydro-2,2-dimethyl-trans-4-(2-oxo-1-pyrrolidinyl)-2H-benzo[b]pyran-3-ol.

In an alternative aspect the present invention provides the use of a compound of the above defined formula (I), or a pharmaceutically acceptable salt thereof, or a pharmaceutically acceptable solvate thereof, for the manufacture of a medicament for the treatment and/or prophylaxis of disorders associated with pulmonary hypertension and/or disorders associated with right heart failure.

It will be appreciated that the said use encompasses all of the abovementioned exemplified, suitable and preferred values of the variables comprising the compounds of formula (I).

In particular the present invention provides the use of a compound of the abovementioned formula (II), or a pharmaceutically acceptable salt thereof, or a pharmaceutically acceptable solvate thereof for the manufacture of a medicament for the treatment and/or prophylaxis of disorders associated with pulmonary hypertension and/or disorders associated with right heart failure.

Examples of a pharmaceutically acceptable salt of a compound of formula (I) include the acid addition salts of a compound of formula (I), wherein one or other of $R_1$ and $R_2$ is amino or an amino-containing group, for example the hydrochloride and hydrobromide salts.

Examples of a pharmaceutically acceptable solvate of a compound of formula (I) include the hydrate.

Preferably, a compound of formula (I) is in substantially pure form.

Examples of the compounds of formula (I) include the examples described in the aftermentioned European Patent Publications.

The compounds of formula (I) may also exist in the form of solvates, preferably hydrates, and the invention extends to the use of such solvates.

The carbon atoms of formula (I) marked with an asterisk "*" are chiral carbon atoms when $R_5$ and $R_6$ do not represent a bond and, for the carbon atom attached the $R_5$, when $R_5$ is other than hydrogen. The carbon atom marked with a double asterisk "**" is chiral when $R_3$ and $R_4$ are different. Thus the compounds of formula (I) may exist in up to eight optical isomeric forms. The present invention extends to the use of all such isomeric forms whether as individual isomers or as mixtures thereof in any proportions, including racemates.

The compounds of formula (I) may also exist in certain geometric isomeric forms. The use of all such forms is encompassed by the present invention, in particular the use of those compounds wherein $R_5$ and $R_6$ do not represent a bond, wherein $R_5$ and the moiety $R_8NCXR_7$ are disposed either mutually cis, with respect to one another or, preferably, mutually trans with respect to one another.

The compounds of formula (I) may be prepared as described in the aforementioned European Publications, in U.S. Pat, Nos. 4,446,113, 4,481,214, 4,496,565, 4,510,152, 4,542,149, 4,555,509, 4,571,406, and 4,575,511 and allowed U.S. Ser. No. 592115, (the subject matter of which are incorporated herein by reference), or by analogous methods thereto.

When used herein the term "pulmonary hypertension" relates to arterial hypertension, capillary hypertension or venous-hypertension.

Suitably, the term "pulmonary hypertension" relates to pulmonary arterial hypertension.

Furthermore it will be understood that pulmonary arterial hypertension relates to both primary arterial hypertension and to pulmonary arterial hypertension occurring secondary to pulmonary diseases such as chronic bronchitis, emphysema, kyphoscoliosis and conditions such as chronic mountain sickness.

When used herein the term "right heart failure" relates to disorders such as cor pulmonale and congenital abnormalities of the heart.

It will be appreciated that cor pulmonale often occurs secondary to certain lung diseases such as chronic bronchitis and emphysema.

Congenital abnormalities of the heart include disorders, such as atrial septal defect, tetralogy of fallot, venticular septal defect and persistent ductus arteriosus.

The administration of a compound of formula (I) or a pharmaceutically acceptable salt thereof may be by way of oral, inhaled or parenteral administration, preferably by inhaled administration.

The active compound may be administered alone or preferably formulated as a pharmaceutical composition.

An amount effective to treat the disorders hereinbefore described depends on the usual factors such as the nature and severity of the disorders being treated and the weight of the mammal. However, a unit dose will normally contain 0.01 to 50 mg for example 0.01 to 10 mg, or 0.05 to 2 mg of the compound of formula (I) or a pharmaceutically acceptable salt thereof. Unit doses will normally be administered once or more than once a day, for example 2, 3, or 4 times a day, more usually 1 to 3 times a day, such that the total daily dose is normally in the range of 0.0001 to 1 mg/kg; thus a suitable total daily dose for a 70 kg adult is 0.01 to 50 mg, for example 0.01 to 10 mg or more usually 0.05 to 10 mg.

It is greatly preferred that the compound of formula (I) or a pharmaceutically acceptable salt thereof is administered in the form of a unit-dose composition, such as a unit dose oral, parenteral, or preferably inhaled composition.

Such compositions are prepared by admixture and are suitably adapted for oral, inhaled or parenteral administration, and as such may be in the form of tablets, capsules, oral liquid preparations, powders, granules, lozenges, reconstitutable powders, injectable and infusable solutions or suspensions or suppositories or aerosols.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

Preferably, compositions for use in this invention are presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns, for example between 1 and 5 microns, such as between 2 and 5 microns.

A favoured inhaled dose will be in the range of 0.05 to 2 mg, for example 0.05 to 0.5 mg, 0.1 to 1 mg or 0.5 to 2 mg.

For parenteral administration, fluid unit dose forms are prepared containing a compound of the present invention and a sterile vehicle. The active compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound. Where appropriate, small amounts of bronchodilators for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

As is common practice, the compositions will usually be accompanied by written or printed directions for use in the medical treatment concerned.

A particularly favoured form of the method of the invention is that wherein the compound of formula (I), or a pharmaceutically acceptable salt thereof, or a pharmaceutically acceptable solvate thereof, is administered by inhalation.

The invention also preferably provides the use of a compound of formula (I), or a pharmaceutically acceptable salt thereof, or a pharmaceutically acceptable solvate thereof, for the manufacture of a medicament for the treatment, by inhalation, of disorders associated with pulmonary hypertension and/or disorders associated with right heart failure.

The present invention further provides a pharmaceutical composition for use in the treatment and/or prophylaxis of disorders associated with pulmonary hypertension and/or disorders associated with right heart failure, which comprises a compound of formula (I) or a pharmaceutically acceptable salt thereof, or a pharmaceutically acceptable solvate thereof, and, if required, a pharmaceutically acceptable carrier therefor.

A particularly favoured pharmaceutically acceptable composition is an inhalation composition, suitably in unit dosage form.

Such compositions may be prepared in the manner as hereinbefore described.

The following pharmacological data illustrate the activity of compounds of formula (I).

Compounds

Compound I is 6-cyano-3,4-dihydro-2,2-dimethyl-trans-4-(2-oxo-1-pyrrolidinyl)-2H-benzo[b]pyran-3-ol. Compound I may be prepared according to the method described in Example 1 of European Patent Publication No. 76075.

Pharmacological Data

Human Isolated Pulmonary Vasculature

Macroscopically normal human lung tissue was obtained from patients undergoing thoracic surgery for bronchial carcinoma. Following surgical removal, the pulmonary arteries were disected into rings and set up in an organ bath under isometric conditions using a 2 g tension. Tissues were allowed to equilibriate for 1h and tone induced with 30 mM potassium chloride. When the contraction had reached a maximum, the inhibitory effect of the test compound was examined in a cumulative protocol fashion ($10^{-8}$ to $2 \times 10^{-5}$M). The results were expressed as a percentage of the maximum relaxation induced by papavarine ($10^{-3}$M).

Results

| Test Compound | $IC_{40}$ |
| --- | --- |
| Compound I | $1.7 \times 10^{-6}$M ± 0.81(n = 6) |

I claim:

1. A method for the treatment or prophylaxis of disorders associated with pulmonary arterial hypertension or disorders associated with right heart failure, in mammals, which method comprises administering to the mammal in need of such treatment or prophylaxis a therapeutically effective or prophylactic, non-toxic, amount of a compound of formula (I):

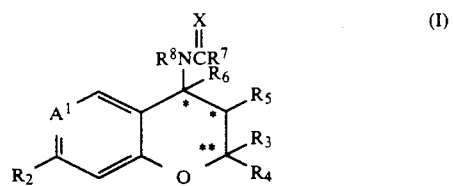

wherein $A^1$ represents $CR_1$, N or $N^+$—$O^-$;
when $A^1$ represents N or $N^+$—$O^-$, $R_2$ represents hydrogen;
when $A^1$ represents $CR_1$ then:
either;
one of $R_1$ and $R_2$ is hydrogen and the other is a group $R^a$ wherein $R^a$ is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino alkylcarbonyl, nitro or cyano, or —C($C_{1-6}$ alkyl)NOH or —C($C_{1-6}$ alkyl)NNH$_2$,
or;
one of $R_1$ and $R_2$ is nitro, cyano or $C_{1-3}$ alkylcarbonyl and the other is a group $R^b$ wherein $R^b$ is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen, hydroxy, $C_{1-6}$ alkoxy or $C_{1-7}$ acyloxy and $R_6$ is hydrogen or $R_5$ and $R_6$ together are a bond;
$R_7$ is hydrogen, $C_{1-6}$ alkyl optionally substituted by hydroxy, $C_{1-6}$ alkoxy, $C_{1-6}$ alkoxycarbonyl or carboxy, $C_{1-6}$ alkyl substituted by halogen, or $C_{2-6}$ alkenyl;aryl or heteroaryl either being optionally substituted by one or more groups or atoms selected from the class of $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl groups;
$R_8$ is hydrogen or $C_{1-6}$ alkyl; or
$R_7$ and $R_8$ are joined together to form $C_{3-4}$ polymethylene or —CH$_2$—(CH$_2$)$_n$—Z—(CH$_2$)m— where m and n represent zero or 1 or 2 such that m+n is 1 or 2, and Z is oxygen, sulphur or $NR_9$ wherein $R_9$ is hydrogen,$C_{1-9}$ alkyl, $C_{2-7}$ alkanoyl, phenyl $C_{1-4}$ alkyl, naphthylcarbonyl, phenylcarbonyl or benzylcarbonyl optionally substituted in the phenyl or naphthyl ring by one or two $C_{1-6}$ alkyl, $C_{1-6}$ alkoxy or halogen;
X is oxygen or sulphur;
or a pharmaceutically acceptable salt thereof, or a pharmaceutically acceptable solvate thereof.

2. A method according to claim 1, wherein, in the compound of formula (I), $A^1$ is $CR_1$.

3. A method according to claim 1, wherein, in the compound of formula (I), when one of $R_1$ and $R_2$ is hydrogen and the other is $R^a$, then $R^a$ is selected from the class of $C_{1-6}$ alkylcarbonyl, $C_{1-6}$ alkoxycarbonyl, nitro or cyano.

4. A method according to claim 1, wherein, in the compound of formula (I), when one of $R_1$ and $R_2$ is hydrogen and the other is $R^a$, then $R^a$ is acetyl, nitro or cyano.

5. A method according to claim 1, wherein, in the compound of formula (I), $R_1$ is $R^a$ and $R^a$ is cyano.

6. A method according to claim 1, wherein, in the compound of formula (I), $R_2$ is hydrogen.

7. A method according to claim 1, wherein, in the compound of formula (I), $R_1$ is $R^a$, $R^a$ is cyano and $R_2$ is hydrogen.

8. A method according to claim 1, wherein, in the compound of formula (I), $R_3$ and $R_4$ are both methyl.

9. A method according to claim 1, wherein, in the compound of formula (I), $R_7$ and $R_8$ together represent $C_3$-polymethylene.

10. A method according to claim 1, wherein, in the compound of formula (I), X is oxygen.

11. A method according to claim 1, wherein the compound of formula (I), is 6-cyano-3,4-dihydro-2,2-dimethyl-trans-4-(2-oxo-1-pyrrolidinyl)-2H-benzo[b]pyran-3-ol.

12. A method according to claim 1, wherein the compound of formula (I), or a pharmaceutically acceptable salt thereof, or a pharmaceutically acceptable solvate thereof, is administered by inhalation.

* * * * *